United States Patent [19]

Aguirre

[11] Patent Number: 4,507,602
[45] Date of Patent: Mar. 26, 1985

[54] MEASUREMENT OF PERMITTIVITY AND PERMEABILITY OF MICROWAVE MATERIALS

[75] Inventor: Donald G. Aguirre, Kirtland AFB, N. Mex.

[73] Assignee: The United States of America as represented by the Secretary of the Air Force, Washington, D.C.

[21] Appl. No.: 407,985

[22] Filed: Aug. 13, 1982

[51] Int. Cl.$^3$ ............................................. G01R 27/04
[52] U.S. Cl. .............................. 324/58 R; 324/58.5 R; 324/58 C
[58] Field of Search .................. 324/58 R, 58 A, 58 B, 324/58 C, 58.5 R, 58.5 A, 58.5 B, 58.5 C, 61 R

[56] References Cited

U.S. PATENT DOCUMENTS 4,361,801 11/1982 Meyer ............................ 324/58.5 R

OTHER PUBLICATIONS

Cohn: "Microwave Measurement of High Dielectric Constant Materials", IEEE Trans. Microwave Theory and Techniques–Sep. 1966–pp. 406–410.

Primary Examiner—Michael J. Tokar
Assistant Examiner—Jose M. Solis
Attorney, Agent, or Firm—Donald J. Singer; Bernard E. Franz

[57] ABSTRACT

Using frequency domain techniques, the system measures the complex permittivity and permeability of different materials in the Ku band (12.4 to 18 GHz). The measuring system comprises a dual horizontal-plane sectoral horn and sample holder assembly. The two horns are placed mouth-to-mouth with the sample holder between them. An input signal is supplied to one horn. The reflected signal from the sample comes back out from the same horn, while the transmitted signal goes through the sample and out via the other horn. The signal source is a frequency synthesizer. A network analyzer and a computer are used to determine the complex permittivity and permeability from the transmission and reflection signals.

6 Claims, 8 Drawing Figures

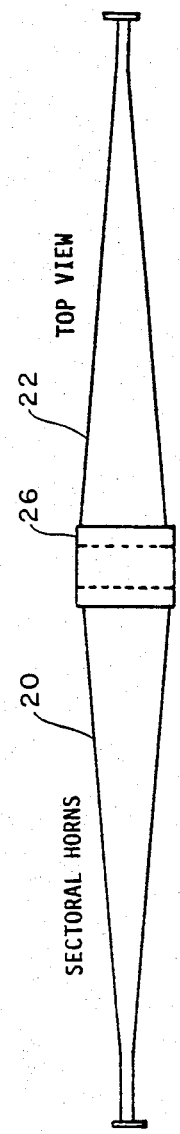
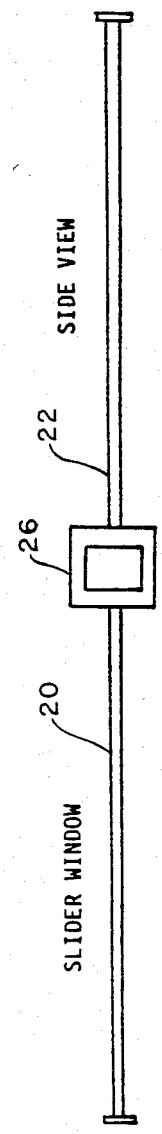
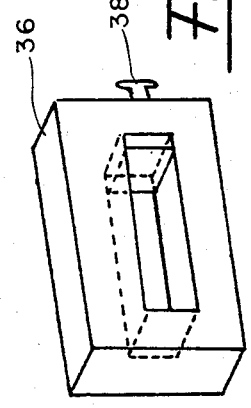
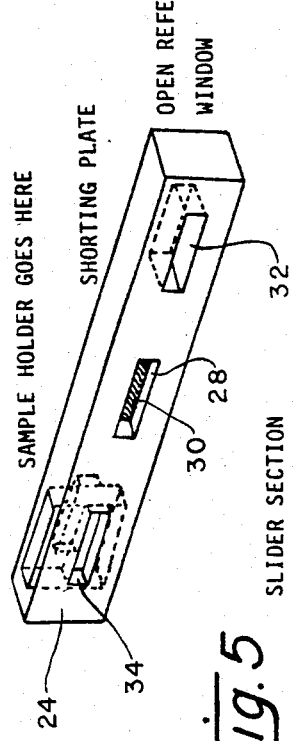
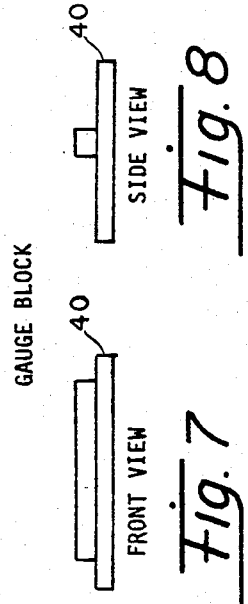
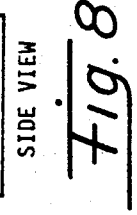

MEASUREMENT OF PERMITTIVITY AND PERMEABILITY OF MICROWAVE MATERIALS

RIGHTS OF THE GOVERNMENT

The invention described herein may be manufactured and used by or for the Government of the United States for all governmental purposes without the payment of any royalty.

BACKGROUND OF THE INVENTION

This invention relates to measurement of permittivity and permeability of different materials, and more particularly to measurement of these properties in radar absorber materials at microwave and millimeter frequencies.

The application of radar absorber materials for concealment of aircraft and missiles hinges on a knowledge of the intrinsic properties of complex permittivity (epsilon) and permeability (mu) of the materials over a wide frequency range. These two properties are a measure of the abilities to conduct electric and magnetic fields which are present in the radar environments. The design and test of the materials depends on the capability to accurately measure the properties. Traditionally, such measurements have been made at fixed frequencies below 10 GHz using slotted-line and impedance-bridge configurations.

SUMMARY OF THE INVENTION

An object of this invention is to provide a technique for measurement of complex permittivity and permeability at frequencies extending into the millimeter wave region up to 100 GHz.

According to the invention, frequency domain techniques are used with a dual sectoral cavity (horn) and a sample holder assembly to measure the reflection and transmission coefficients of a sample. The two sectoral horns are placed mouth to mouth, and connected at the sample holder area. The measurement equipment includes a signal source, a network analyzer used for making relative decibel amplitude and phase measurements, and a computer to control the measurement setup.

There are three windows cut along the length of a slider section constituting the sample holder. One window has a shorting plate of stainless steel used to obtain the reference for making reflection coefficient measurements. Another window is open, used to obtain the reference for making transmission coefficient measurements. The third window is used to hold the sample during measurements.

BRIEF DESCRIPTION OF THE DRAWING

FIGS. 3 and 4 are top and side views respectively of a dual sectoral horn assembly;

FIG. 5 is a perspective view of the slider section;

FIG. 6 is a perspective view of the sample holder; and

FIGS. 7 and 8 are front and side views respectively of a gauge block used in mounting a sample in the sample holder.

DETAILED DESCRIPTION

Figure 1:
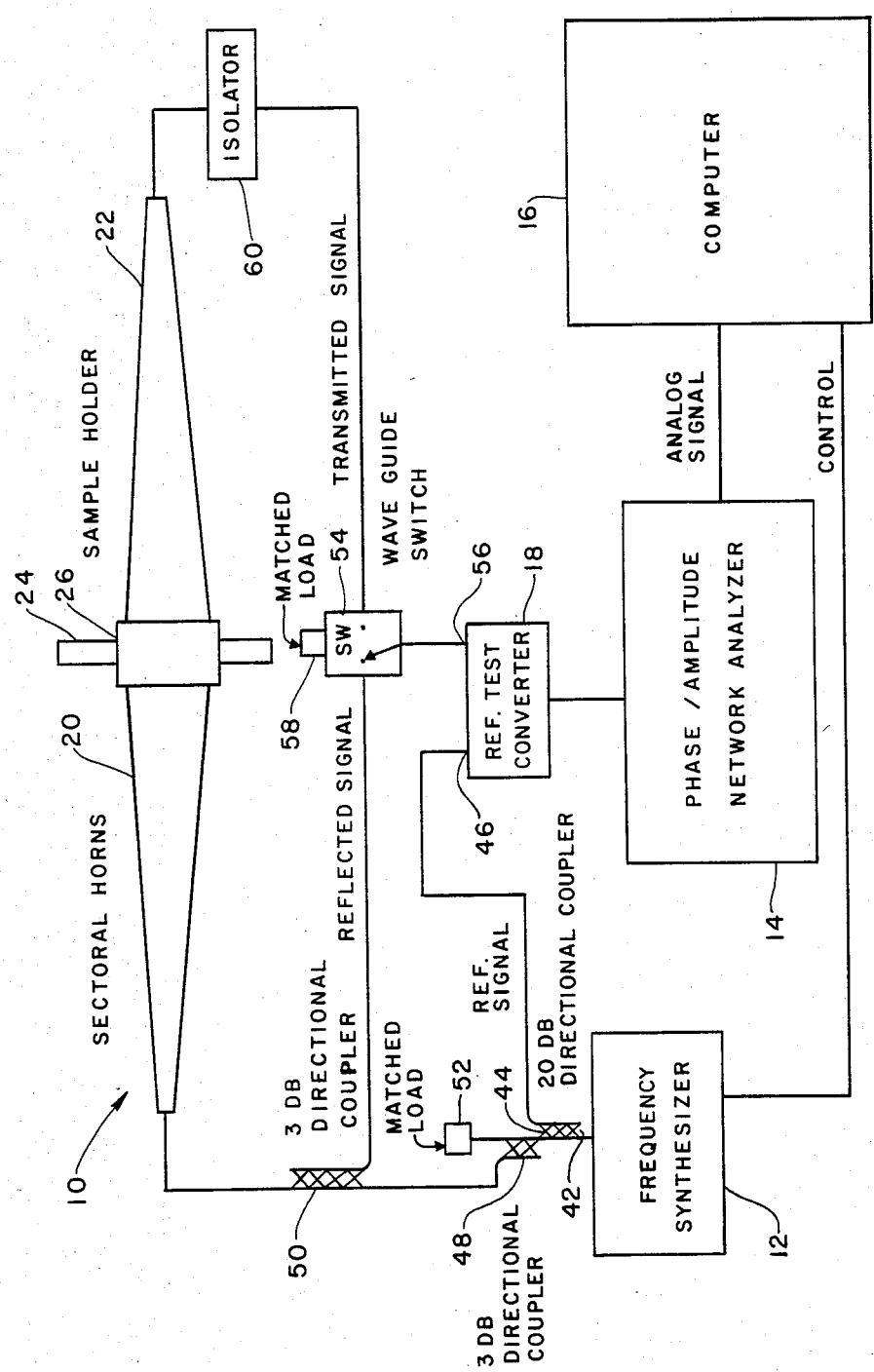
FIG. 1 is a block diagram of a frequency domain measurement system.

The invention is described in my thesis titled "Frequency Domain Measurements of Microwave Absorber Design Materials" (AFIT/GE/80D-8), presented to the faculty of the School of Engineering of the Air Force Institute of Technology, Air University, United States Air Force. The thesis is available from the National Technical Information Service (NTIS) under the AD Number A100764, and is incorporated herein and made a part hereof as though fully set forth.

The ability to design and test radar absorber design materials depends on the capability to accurately measure the intrinsic properties of complex mu and epsilon of the material over a wide frequency range. There was an earlier project to build a time domain measurement system that could measure complex mu and epsilon parameters of design materials over a frequency range from 0.1 to 16 GHz. Traditionally, such measurements have been made at fixed frequencies below 10 GHz using slotted-line and impedance-bridge configurations.

Essentially, the time domain measurement system consists of a sub-nanosecond pulse generator and coaxial line system to hold samples of materials, a wideband sampling oscilloscope, and an electronic system which scans and digitizes the transient response of microwave materials. The transient response is then Fourier transformed on a Hewlett-Packard 21MX computer to provide frequency domain scattering coefficients. Further computation provides printouts and graphs of complex mu and complex epsilon as a function of frequency. Although the time domain system works well, there is a need for a measurement capability of complex permittivity and permeability of candidate design materials at frequencies higher than 16 GHz.

The National Bureau of Standards published a report dealing with radar absorber design material measurement techniques at frequencies above 20 GHz. One area of the report reviews the existing time domain measurement system and recommends a frequency domain approach as one possible way to extend the mu and epsilon measurement capability into the millimeter frequency range. This would involve the development and verification of a frequency domain technique that can be integrated into the present time domain measurement system with the minimum equipment modification possible. The time domain system uses two specialized generators. One of these generators produces a very narrow and sharp impulse-like signal, whose spectral content is primarily in the frequency range from 0.1 to 10 GHz. The second generator emits a radio frequency burst, whose spectral content is between 9 and 16 GHz. Utilizing these two generators, two measurements then characterize the permeability and permittivity of a sample from 0.1 to 16 GHz. A sampling oscilloscope is used to sample the transient response for digitizing, so that scattering parameters can be computed at discrete frequencies.

The technological limitations of the sampling oscilloscope provides the impetus to develop a frequency domain measurement system. The frequency domain approach would delete the requirement for the two special radio frequency generators and instead utilize a continuous wave generator, frequency synthesizer, tuned from discrete frequency to discrete frequency. The continuous wave radio frequency signals would also negate the requirement for sampling the transient signal response. Instead, the reflected and transmitted signals would be at a set frequency and could be digitized and processed using analog-to-digital (A/D) techniques.

Problem and Scope

The problem addressed in the thesis is that of experimentally developing a millimeter frequency domain measurement system, and demonstrating the system capabilities by measuring the intrinsic properties of several common materials at the Ku band (12.4 to 18 GHz). Existing material properties obtained from the time domain system can be used for comparison. The computer code should be modified to automate the measurement process by putting the frequency synthesizer under computer control and reading the network analyzer phase and amplitude outputs with the computer's A/D converter.

After demonstration of the concept feasibility, the measurement setup can be modified to apply the technique at frequencies between 20 and 100 GHz.

The thesis contains a description of the fully automated frequency domain measurement system and data comparisons for fiberglass, two thicknesses of plexiglas, Teflon, and FGM-40 absorber materials measured in both the time domain and the frequency domain systems. The frequency domain measurement system is depicted in FIG. 1. The frequency domain setup consists of two H-plane sectoral horns (Barrow and Chu, 1939) which are placed mouth to mouth. The system is used to measure the reflection and transmission coefficients from a single rectangular sample of the design material.

Five specific samples were evaluated, fiberglas, two thicknesses of plexiglas, teflon, and an FGM-40 absorber. To show concept feasibility, data were compared for the five samples tested on both the time domain system and the frequency domain system. The samples prepared for use in the time domain system were of such small dimension that a good uniformity of thickness could be expected; however, samples used in the frequency domain system were larger (7.60 sq cm) and were subject to slight nonuniformity of thickness. Therefore, the thickness value used for the computation of relative mu and epsilon in the frequency domain system is the average thickness across the sample.

The H-plane sectoral horn assembly is assumed to produce a transverse electromagnetic plane wavefront at the sample interface. The plane wavefront approximation was sought because it provides a means to calculate mu and epsilon values using relatively uncomplicated mathematics.

Assumptions

In the frequency domain measurement setup, it will be assumed that the electromagnetic fields normally incident on the sample material interface approximate a plane wave. This assumption is discussed in the theory section of the thesis. The theoretical phase variation in the mouth of the H-plane sectoral horn ranges from 11.8° at 12.4 GHz to 16.24° at 18 GHz, using the dimensions of $L_h = 150$ cm and $a = 9.5$ cm in the equation $$\Delta\phi = \left[ \frac{a^2}{8\lambda L_h} \right] 360°$$

(Jasik, 1961).

General Approach

1. The existing time domain measurement system was studied.
2. Literature material associated with the sample holder, network analyzer, frequency synthesizer, and waveguide components used in the measurement system was analyzed.
3. An initial determination of the test setup and the actual assembly of the test system was performed.
4. The existing time domain computer program to delete portions of code associated with the Fourier Transform was modified and computer code was added to accept the frequency domain measured values as input.
5. The test setup, putting the frequency synthesizer under computer control and reading the network analyzer's phase and amplitude outputs through the computer's A/D converter was automated.
6. The sample materials were measured and mu and epsilon from both the time domain and frequency domain systems were compared.
7. The ideas developed in building the test system were extended and a final frequency domain system that could measure reflection and transmission coefficients from a single, small sample was designed and built.
8. The measured values of mu and epsilon from the final frequency domain system were taken and compared to data obtained from the time domain system.

Sequence of Presentation

The material in the thesis is presented in the following manner:

1. The theory underlying the measurement technique is presented in Section II.
2. A description of the equipment used in the frequency domain setup is given in Section III.
3. The sample measurement procedures are presented in Section IV.
4. The results are given in Section V.
5. Finally, the conclusions and recommendations are presented in Section VI.

For a presentation of the theory, results, and conclusion sections, as well as control software, reference is made to the thesis.

Equipment

During the course of this work, there were two operating systems developed. The first system was a test setup and used an anechoic chamber and a modified H-plane sectoral horn to measure the transmission and reflection coefficients, respectively. A full description of this setup is provided in Appendix B of the thesis. The second system utilizes the two H-plane sectoral horns. It is this second system which is reported on in the main body of the thesis.

The major pieces of equipment used in the frequency domain measurement system will be described first. Then a full description of how these major pieces of equipment are assembled for intrinsic property measurements will be given.

The equipment used (FIG. 1) consisted of a frequency synthesizer 12 which served as the signal source, a network analyzer 14 used for making relative decibel amplitude and phase measurements, a two-sectoral horn assembly 10 and sample holder used to measure reflection and transmission coefficient parameters, and a Hewlett-Packard 21MX RTE computer 16 used to control the measurement setup. The complete measurement setup is diagrammed in FIG. 1.

Frequency Synthesizer

The signal source 12 is a Watkins and Johnson model 1204-1; rapidly tunable over a frequency range of 0.1 to 26 GHz. The following information was taken from the Watkins and Johnson 1204-1 specification sheet. The frequency resolution is 10 kHz from 100 MHz to 249.99 MHz, 100 kHz from 250 MHz to 1.9999 GHz, and 1 MHz from 2–26 GHz. The frequency is displayed with a five-digit LED, in GHz, with floating decimal. The frequency accuracy is ±0.00035% for 180 days over a 0°–50° C. range. A single frequency can be selected on the keyboard with the enter, ENT, button and displayed on the LED. The frequency can be slewed up or down in 1, 10, and 100 MHz steps as selected on the INCREMENT controls. The synthesizer sweeps repetitively upward within the following bands: 0.1–1 GHz, 1–2 GHz, 2–8 GHz, 8–13 GHz, 13–18 GHz, and 18–26 GHz. The $\Delta F$ symmetrical sweep about phase-locked center frequency F which is displayed on the LED readout is 0 to ±0.1% of F. The synthesizer provides 0 dBm (1 mw) minimum leveled output power. The variations in leveled power for the 0 dB attenuator setting is ±1 dB over the range of 0.1–26 GHz. The output power can be attenuated over a range of 0 to 90 dB in 10 dB steps. The output power accuracy (meter reading plus attenuator setting) is: 0 dB attenuator setting, 0.1–18 GHz, ±1 dB and 18–26 GHz, ±1 dB; 10 dB-90 dB attenuator setting, ±2 dB and 18–26 GHz, ±2.5 dB.

Network Analyzer

The network analyzer 14 is a Hewlett-Packard Model 8410A with a phase-gain indicator. The 8413A phase-gain indicator uses a meter display. The 8411A harmonic frequency converter 18 provides RF-to-IF conversion. The 8411A converter has been modified under Option 018 to work across the Ku band. The VSWR at the reference and test port under Option 018 increases to 10 at 18 GHz. Measurements are based on the use of two wideband samplers to convert the input frequencies to a constant IF frequency. RF-to-IF conversion takes place entirely in the harmonic frequency converter, which converts frequencies over a range of 12.4–18 GHz to 20 MHz IF signals. The phase and amplitude of the two RF input signals are maintained in the IF signal. The network analyzer 14 mainframe provides the phase-lock circuitry to maintain the 20 MHz IF frequency while frequency is being swept, takes the ratio of the reference and test channels by use of identical AGC amplifiers, and then converts down to a second IF at 278 kHz. It also has a precision 0 to 69 dB IF attenuator with 10 and 1 dB steps for accurate IF substitution measurements of gain or attenuation. The frequency domain measurement setup utilized the following piece of equipment during data measurements: a plug-in for the 8410A mainframe, the 8413A phase-gain indicator. It compares the amplitudes of the two IF signals and provides a meter readout of their ratio directly in dB with 0.1 dB resolution. It also compares phase in degrees over a 360° unambiguous range with 0.2° resolution on the meter. Phase difference is presented on the same meter when the appropriate function button is depressed. This plug-in has two analog output ports accessible from the front, one for dB amplitude, 20 mv/dB, and one for phase, 50 mv/degree.

Horn Assembly

Figure 2:
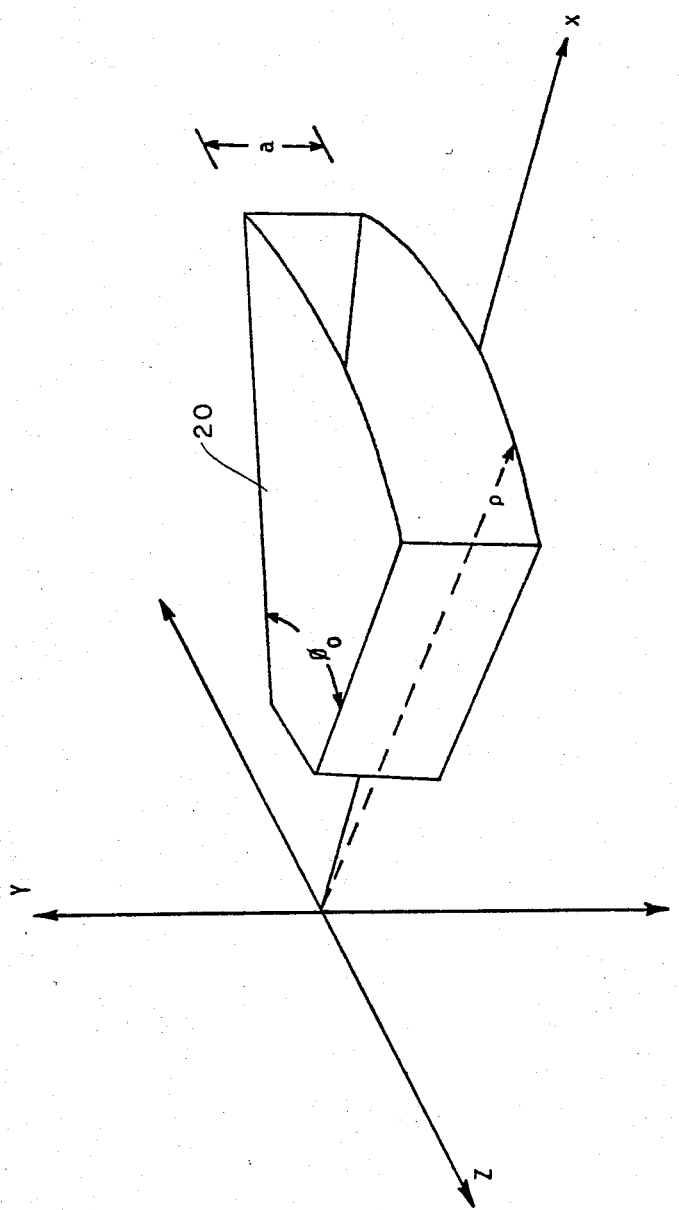
FIG. 2 is a perspective view of one sectoral horn, showing a cylindrical coordinate system.

A sectoral horn 20 and cylindrical coordinate system for analysis is shown in FIG. 2. The H-plane sectoral horn assembly 10 and sample holder in FIG. 1 is constructed from aluminum. There are three major parts comprising this assembly. The two horns 20 and 22, the sample holder/reference slide section 24, and the sample holder itself. The individual pieces are depicted in FIGS. 3–6.

The two sectoral horns 20 and 22 are placed mouth to mouth and form the central part of the measurement system. The full length of the horn section is 310.5 cm. The inner dimensions at the end flange region are 1.6 cm×0.8 cm, and at the mouth 9.5 cm×0.8 cm. The two horns are connected at the sample holder area.

The sample holder section is made up of a 6 cm×5 cm×15 cm solid block slider 24 which fits inside the 10.5 cm×11 cm×15 cm rectangular housing 26. There are three windows cut along the length of the slider section. In the center window 28, the slider section has a shorting plate 30 made of stainless steel used to obtain the reference for making reflection coefficient measurements. At one end of the slider, there is an open rectangular window 32 measuring 9.5 cm×0.8 cm which is used to obtain the reference for making transmission coefficient measurements. The third window 34 is used to hold the sample during measurement.

The sample holder 36 is removed from the slider section during sample installation. The overall dimensions of the sample holder are 11.3 cm×5 cm×3 cm. A 9.5 cm×0.8 cm window in the sample holder serves to accommodate the sample. A set screw 38 at one side is used to apply a small amount of pressure on the sample to hold it in place so it does not become misaligned during installation of the sample holder in the slider.

A gauge block is used when mounting the sample material into the sample holder. The gauge block 40 (front view in FIG. 7 and side view in FIG. 8) provides a means to position the sample's front face at the same plane as the shorting plate for reflection coefficient measurements. The sample holder 36 is placed on the gauge block with the 1.119 cm raised section inserted in the sample window. The sample is placed in the sample window and forced firmly against the raised section as the set screw is tightened.

21MX Computer

The Hewlett-Packard 21MX computer 16 is used to control the data measurement. The frequency synthesizer 12 is commanded to a discrete frequency by the computer and a data measurement taken through the computer A/D converter connected to the outputs of the network analyzer 14. The disk subsystem and I/O devices are used to store, process, and display the results of a data run. The computer software is provided in Appendix A of the thesis.

With some insight into the main parts of the frequency domain measurement system, the rest of this chapter will deal with discribing the system as a whole and how it is interconnected. This description is an amplification of FIG. 1.

Measurement System

The Watkins and Johnson 1204-1 Synthesizer serves as the signal source. It is commanded by the 21MX computer to discrete frequencies as part of the intrinsic property measurement routine. The RF signal is routed from the signal synthesizer to the Ku band wave guide by means of a six-foot coaxial cable 42 (C1803-72 B&W Associates, Inc., Burlington, MA). The cable 42 connects into a Narda 4609, 12.4 to 18 GHz, coaxial to wave guide adapter (not shown). The Narda adapter is attached to a 20 dB Hewlett-Packard (HP directional coupler 44, model number P752D. The 20 dB coupler 44 couples a portion of the signal into the reference port 46 of the HP 8411 Harmonic Frequency Converter 18 (modified with Option 018 to extend its capability from 12.4 to 18 GHz). The main RF signal is fed into a second directional coupler 48. This second HP directional coupler, Model P752A, couples 3 dB of the signal into a third directional coupler 50 and sends the rest of the signal into a matched load 52. The third HP coupler 50, model number P752A, is used to couple 3 dB of reflected signal from the sample or short into an FXR model Y641A switch 54 and then into the test port 56 of the harmonic frequency converter 18 during reflection coefficient measurements. During transmission coefficient measurements, any reflected signal coupled through this 3 dB coupler is switched into a Waveline Type 754 matched load 58.

For transmission coefficient measurements, the RF signal which transmits through the sample is routed into the test port 56 of the harmonic frequency converter 18 through a PRD Electronics, Inc., Type 1208 Isolator 60 and the switch 54. The transmitted signal through the sample is terminated in a matched load at the switch during reflection coefficient measurements.

The harmonic frequency converter 18 provides the IF signal to the HP 8410B Network Analyzer 14. The analog amplitude and phase ports on the front of the HP 8413A Phase-Gain Indicator are read by the computer. An HP Plug-In 20 KHz Analog-to-Digital Interface Subsystem located in the 21MX computer, machine model HP2108A, converts the analog inputs to digital values used for computation. A Tektronix 4006-1 CRT Terminal is the operator control center for sample measurements. Finally, the processed mu and epsilon data are routed from the computer to the HP 2635A Line Printer or, for plots of mu and epsilon, to the Tektronix 4631 Hard Copy Unit.

Procedure

1 The sample is prepared by cutting a 9.5×0.8 cm rectangular piece from the material to be measured.

1a. The sample is cut to fill the sample window completely.

1b. The thickness of the sample in mils is determined for use in the computer program.

2. The frequency synthesizer and network analyzer are turned on for a half hour before any measurements are to be taken.

3. The frequency synthesizer and network analyzer are adjusted for making measurements. The slider section in the sample holder assembly is positioned with the shorting plate in the sectoral horn and the reflected signal line is switched to the test port of the harmonic frequency converter as shown in FIG. 1.

3a. The local/remote switch at the back of the frequency synthesizer is placed in local.

3b. The Ku band midrange frequency of 15 GHz is entered at the frequency synthesizer keyboard and the output signal power level is set to +3 dbm.

3c. The network analyzer is adjusted to read 0 dB on the 3 dB amplitude scale by means of the amplitude vernier and the amplitude gain amplifier.

3d. The amplitude meter is switched to the 30 dB scale and an additional 30 dB is added to the test signal amplitude.

3e. The phase offset dial on the network analyzer is placed at +20°. This value is arbitrary since the coefficient phase measurements are only difference values between a reference phase and the phase associated with reflections off and transmissions through the sample.

3f. The local/remote switch on the frequency synthesizer is set to remote. This mode enables communications between the computer and frequency synthesizer.

4. The computer program is initiated and a statement about the sample is typed in for use as a heading on the relative mu/ epsilon output data at the line printer.

4a. The sample thickness in mils is entered for use in calculating the relative mu/epsilon data of the sample.

4b. The beginning and ending frequencies in GHz are entered next.

4c. The number of frequencies to be measured is entered. The frequency increment is determined in the computer routine by the equation $$\Delta F = \frac{\text{End Frequency} - \text{Start Frequency}}{\text{No. of Frequencies to be Measured} - 1}$$

This routine allows the first frequency measured to be the start frequency.

4d. The main command listing is displayed on the CRT and the characteristic of the system can now be measured.

5. Under ideal conditions, the relative mu and epsilon values are determined using the free space values $\mu_o$ and $\epsilon_o$. However, it is possible to measure a $\mu_o$ and so value for the frequency domain system which has slight deviations from the free space values. These new measured values of $\mu_o$ and $\epsilon_o$ can be complex and characterize how well the frequency domain measurement system approximates free space. A typical plot of $\mu_o$ and $\epsilon_o$ characterizing the measurement system is given in FIG. 6A and 6B of the thesis. The system measured values of $\mu_o$ and $\epsilon_o$ are used to renormalize the relative mu and epsilon data calculated for the sample prior to output.

5a. The sample holder with no sample installed is used in the system characteristic measurement.

5b. The shorting plate is placed at the center of the horn assembly and the reflection signal line is switched into the test port of the harmonic frequency converter.

5c. The reflection coefficient measurement routine is entered and the reference values are measured and stored.

5d. At the end of the reference measurement routine, the sample holder window is placed at the center of the horn assembly and the sample measurement routine entered.

5e. At the end of the sample measurement routine, the computer has calculated and stored the reflection coefficient values.

5f. At this time, the slider is repositioned with the open reference window at the center of the horn assembly and the transmission signal line is switched into the test port of the harmonic frequency converter.

5g. The transmission coefficient measurement routine is entered and the reference values through the open window are measured and stored.

5h. When the reference measurements are complete, the sample window is again slid to the center of the horn assembly and the sample measurement routine entered. The transmission coefficient is calculated and stored.

5i. At this point, the mu/epsilon calculation routine is entered. During this calculation, the thickness value used for computation of mu and epsilon is 200 mils if this is the first measurement run after entering the program. If this is not the first measurement run after entering the program, the thickness value used for calculation is that thickness entered at the beginning of the program for the sample.

5j. The system characteristic values are stored for renormalization of sample relative mu and epsilon values.

6. The reflection coefficient measurement routine is re-entered and the sample to be measured is installed in the sample holder.

6a. The sample holder is removed from the slider section and placed on the gauge block with the raised section inserted in the sample window such that the set screw is to the right. The sample is inserted and pressed firmly against the raised section of the gauge block. The set screw is adjusted to hold the sample lightly.

6b. The sample holder is re-installed in the slider section with the set screw away from the shorting plate.

6c. The mu and epsilon values are determined by following the steps from 6b to 5i.

7. The relative mu and epsilon values calculated for the sample are renormalized and then routed as numeric data output to the line printer or as plots to the hard copy unit. When the plot option is used to display the output data, a statement about the sample must be entered to serve as a title for the plots.

SUMMARY

Using frequency domain techniques, a system was developed to measure the complex permittivity and permeability of different materials in the Ku band (12.4 to 18 GHz). A sample of fiberglass, teflon, FGM-40, and two different plexiglas configurations were chosen for this experiment. The newly developed measuring system consisted of a two horizontal-plane sectoral horn and a sample holder assembly. A 9.5×0.8 cm piece of the sample material was cut and fitted into the sample holder assembly. The reflection and transmission coefficients for the sample were measured, using a network analyzer and frequency synthesizer as the swept frequency signal source. A dedicated computer calculated the complex permittivity and permeability and plotted the output data. The measurements were performed automatically by having the computer control the frequency synthesizer while running the experiment.

The two configurations of plexiglas and the fiberglass sample were tested ten times to obtain a statistical representation of the results. In all cases good repeatability was obtained. The standard deviation of the real part of the permittivity and permeability for the two cases of plexiglas was within ±4% of the mean. The fiberglass had a typical standard deviation within ±7% of the mean for the real part of the permittivity and permeability.

The permittivity and permeability obtained for the selected samples using the frequency domain measurement technique were compared with the results obtained in a previously developed system which used time domain techniques. The data comparison between the two systems was good for teflon, plexiglas, and fiberglass in the frequency range from 12.4 to 16 GHz. Some variations were noted for the FGM-40. Since the results obtained were generally consistent between both techniques, it is claimed that the newly implemented frequency domain system is a viable alternative for the rapid measurement of intrinsic properties in the Ku band.

Thus, while preferred constructional features of the invention are embodied in the structure illustrated herein, it is to be understood that changes and variations may be made by the skilled in the art without departing from the spirit and scope of my invention.

I claim:

1. The method of measuring complex permittivity and permeability at millimeter wavelengths with frequencies extending into the region above 16 gigahertz, and capable of application at frequencies between 20 and 100 gigahertz, using apparatus comprising first and second horns, each horn being a horizontal sectoral horn having a throat at one end and having one pair of sides diverging to a mouth at a wider end, the other pair of sides being parallel, the two horns being placed mouth-to-mouth with means for placing a sample of material between them, means for supplying a continuous wave signal at a set frequency to the first horn, so that the signal propagates in the first horn to the sample; part of the signal energy being reflected from the sample and returned to the throat of the first horn, and part being transmitted through the sample and the second horn to its throat;

wherein said means for placing a sample comprises a housing between the mouths of the two horns, the housing having an opening transverse to the horns, a slider section which fits into the opening, the slider section having first, second and third windows, each window having an area with dimensions substantially the same as the mouths of the horns, the first window having a shorting plate to obtain a reference for making reflection coefficient measurements, the second window beign open to obtain a reference for making transmission coefficient measurements, the third window being used to hold the sample;

a sample holder for holding the sample, the sample holder being adapted for insertion into the third window;

a phase/amplitude network analyzer which produces analog output signals, a computer coupled to receive the output signals from the network analyzer, the computer having means to digitize the last said signals and being programmed to compute the complex permittivity and permeability;

a frequency synthesizer for generating said continuous wave signal, with means for the computer to step the frequency synthesizer to successively set frequencies within a given range;

a reference test converter having a reference port, a test port, and an output port, the output port being coupled to the network analyzer, the output of the frequency synthesizer being coupled via a first directional coupler to said reference port, the output of the frequency synthesizer being also coupled via a second directional coupler to the throat of the first horn, a wave guide switch having one input coupled via a third direction coupler to the throat of the first horn for reflected signals, the wave guide switch having a second input coupled via an isolator to the throat of the second horn for transmitted signals, and the output of the wave guide switch being coupled to said test port, RF signals at the test port being converted to signals at a fixed IF frequency for use by the network analyzer;

wherein said method comprises the steps:
  a. using the sample holder with no sample installed in a system characteristic measurement;
  b. placing the shorting plate at the center of said housing and switching the reflection signal line into said test port;
  c. using a reflection coefficient measurement routine to measure and store reference values;
  d. placing the sample holder window at the center of said housing and entering a sample measurement routine;
  e. the computer operating to calculate and store the reflection coefficient values;
  f. repositioning the slider section with the second (open reference) window at the center of said housing and switching the transmission signal line into said test port;
  g. entering a transmission coefficient measurement routine so that reference values through the open window are measured;
  h. when the reference measurements are complete, again placing the third (sample holder) window at the center of said housing and entering the sample measurement routine so that the transmission coefficient is calculated and stored;
  i. entering a mu/epsilon calculation routine;
  j. the computer operating to calculate and store characteristic values for renormalization of sample relative mu and epsilon values;
  k. entering a reflection coefficient measurement routine and placing the sample to be measured in the sample holder, using a gauge block to position the sample's front face at the same plane as the shorting plate for reflection coefficient measurements, the sample holder being reinstalled in the slider section; and
  l. determining the mu and epsilon values by following steps b through i.

2. The method as set forth in claim 1, further including preliminary steps comprising:
  preparing the sample by cutting a rectangular piece from the material to be measured, the sample being cut to fill the sample window completely;
  determining the thickness of the sample and entering the value in the computer;
  entering values relating to the frequency range and the number of discrete frequencies to be measured, and computing the delta frequency between runs;
  during the mu/epsilon calculation routine (step i), the thickness value used for computation of mu and epsilon being a predetermined value for the first measurement run after entering the program, and in subsequent runs after entering the program, the thickness value used for calculation being that thickness previously entered for the sample.

3. Apparatus for measuring the complex permittivity and permeability of different materials at millimeter wavelengths with frequencies extending into a region above 16 gigahertz, comprising first and second horns, each horn being a horizontal sectoral horn having a throat at one end and having one pair of sides diverging to a mouth at a wider end, the other pair of sides being parallel, the two horns being placed mouth-to-mouth with means for placing a sample of material between them, means for supplying a continuous wave signal at a set frequency to the first horn, so that the signal propagates in the first horn to the sample; part of the signal energy being reflected from the sample and returned to the throat of the first horn, and part being transmitted through the sample and the second horn to its throat, and means for alternatively supplying the reflected signal from the throat of the first horn and the transmitted signal from the throat of the second horn to equipment for analysis to determine the complex permittivity and permeability;

wherein said means for placing a sample comprises a housing between the mouths of the two horns, the housing having an opening transverse to the horns, a slider section which fits into the opening, the slider section having first, second and third windows, the first window having a shorting plate to obtain a reference for making reflection coefficient measurements, the second window being open to obtain a reference for making transmission coefficient measurements, the third window being used to hold the sample;
  a sample holder for holding the sample, the sample holder being adapted for insertion into the third window, and a gauge block for use in properly locating the sample in the sample holder.

4. Apparatus as set forth in claim 3, wherein said equipment includes a phase/amplitude network analyzer which produces analog output signals, and a computer coupled to receive the output signals from the network analyzer, the computer having means to digitize the last said signals and being programmed to compute the complex permittivity and permeability.

5. Apparatus as set forth in claim 4, which includes a frequency synthesizer for generating said continuous wave signal, with means for the computer to step the frequency synthesizer to successively set frequencies within a given range.

6. Apparatus as set forth in claim 5, further including a reference test converter having a reference port, a test port, and an output port, the output port being coupled to the network analyzer, the output of the frequency synthesizer being coupled via a first directional coupler to said reference port, the output of the frequency synthesizer being also coupled via a second directional coupler to the throat of the first horn, a wave guide switch having one input coupled via a third directional coupler to the throat of the first horn for reflected signals, the wave guide switch having input coupled via an isolator to the throat of the second horn for transmitted signals, and the output of the wave guide switch being coupled to said test port, RF signals at the test port being converted to signals at a fixed IF frequency for use by the network analyzer.

* * * * *